US012789334B2

(12) United States Patent
Arazawa et al.

(10) Patent No.: US 12,789,334 B2
(45) Date of Patent: Nov. 10, 2026

(54) LOCKING DEVICES AND MECHANISMS FOR TORQUE-LIMITING DEVICES

(71) Applicant: ECA Medical Instruments, Inc., Thousand Oaks, CA (US)

(72) Inventors: Alexander Arazawa, Thousand Oaks, CA (US); Navid Mahpeykar, Thousand Oaks, CA (US); Andre Comella, Thousand Oaks, CA (US); Tommy Tak, Thousand Oaks, CA (US)

(73) Assignee: ECA Medical Instruments, Thousand Oaks, CA (US)

( * ) Notice: Subject to any disclaimer, the term of this patent is extended or adjusted under 35 U.S.C. 154(b) by 266 days.

(21) Appl. No.: 18/634,053

(22) Filed: Apr. 12, 2024

(65) Prior Publication Data

US 2024/0342876 A1 Oct. 17, 2024

Related U.S. Application Data

(60) Provisional application No. 63/458,797, filed on Apr. 12, 2023.

(51) Int. Cl.
*B25B 23/14* (2006.01)
*A61B 90/00* (2016.01)

(52) U.S. Cl.
CPC ............ *B25B 23/141* (2013.01); *A61B 90/03* (2016.02); *A61B 2090/031* (2016.02)

(58) Field of Classification Search
CPC ... B25B 23/14; B25B 23/141; B25B 23/1415; B25B 21/00; B25B 21/007; B25B 27/143; F16B 31/021; A61B 90/03; A61B 2090/031
USPC ................................................ 411/4; 81/53.2
See application file for complete search history.

(56) References Cited

U.S. PATENT DOCUMENTS

| | | | | | |
|---|---|---|---|---|---|
| 1,009,248 | A * | 11/1911 | Jenkins | B25B 13/48 | 81/53.2 |
| 1,030,732 | A * | 6/1912 | Jenkins | B25B 13/48 | 81/53.2 |
| 1,298,324 | A * | 3/1919 | Funk | B25B 23/103 | 81/53.2 |
| 2,421,181 | A * | 5/1947 | Batchelder | F16B 35/042 | 81/436 |
| 2,728,252 | A * | 12/1955 | Connell | B25B 23/141 | 81/475 |
| 2,842,180 | A | 7/1958 | Brown | | |

(Continued)

FOREIGN PATENT DOCUMENTS

WO 2023012119 A1 2/2023

OTHER PUBLICATIONS

International Search Report and Written Opinion issued in App. No. PCT/US24/24307, dated Sep. 6, 2024, 13 pages.

*Primary Examiner* — David B. Thomas
(74) *Attorney, Agent, or Firm* — Ferguson Case Orr Paterson LLP

(57) ABSTRACT

The present disclosure relates generally to locking mechanisms for torque-limiting devices. Some devices, methods, and systems disclosed herein include a threaded component, wherein said threaded component is configured with a hole that runs through said component; and a lock defining an opening at one end and a hole at the other end, wherein said opening is configured to enclose said threaded component and align said hole of said threaded component and said hole of said lock.

15 Claims, 12 Drawing Sheets

(56) References Cited

U.S. PATENT DOCUMENTS

| | | | | | |
|---|---|---|---|---|---|
| 2,906,152 | A * | 9/1959 | Brase | B25B 13/48 | 81/53.2 |
| 3,191,486 | A | 6/1965 | Gibbens | | |
| 3,285,119 | A * | 11/1966 | Dean | F16B 23/0061 | 81/436 |
| 3,369,441 | A * | 2/1968 | Kosar | F16B 23/0046 | 81/436 |
| 3,412,773 | A * | 11/1968 | Breed | F16B 39/30 | 411/938 |
| 3,460,428 | A * | 8/1969 | Charles | F16B 31/021 | 29/446 |
| 3,587,701 | A * | 6/1971 | Gold | F16B 39/284 | 411/281 |
| 3,662,628 | A * | 5/1972 | Schnepel | B25B 23/141 | 464/36 |
| 4,068,555 | A | 1/1978 | Volkman | | |
| 4,144,796 | A * | 3/1979 | Richter | F16B 31/021 | 411/4 |
| 4,215,600 | A * | 8/1980 | Kesselman | B25B 23/1415 | 81/471 |
| 4,262,501 | A * | 4/1981 | Vaughn | F16D 7/08 | 464/36 |
| 4,472,098 | A | 9/1984 | Kiefer | | |
| 4,572,041 | A * | 2/1986 | Rissmann | F16D 7/048 | 464/37 |
| 4,653,358 | A * | 3/1987 | Lankry | B25B 23/0064 | 81/429 |
| 4,684,138 | A * | 8/1987 | Michaud | B25B 27/18 | 81/53.2 |
| 4,823,653 | A * | 4/1989 | Batten | F16B 39/02 | 81/468 |
| 4,836,727 | A * | 6/1989 | Volkmann | F16B 31/021 | 411/432 |
| 4,867,624 | A | 9/1989 | Walley | | |
| 4,881,316 | A * | 11/1989 | Wing | B25B 13/065 | 29/517 |
| 4,971,156 | A * | 11/1990 | Wong | F16H 3/24 | 74/340 |
| 5,017,079 | A * | 5/1991 | Reynolds | F16B 39/284 | 411/432 |
| 5,049,017 | A * | 9/1991 | Reynolds | F16B 39/284 | 411/222 |
| 5,176,050 | A * | 1/1993 | Sauer | F16B 31/021 | 81/180.1 |
| 5,297,458 | A * | 3/1994 | Smith | B25B 13/06 | 81/124.2 |
| 5,299,474 | A * | 4/1994 | Hohmann | F16B 31/021 | 81/467 |
| 5,520,076 | A * | 5/1996 | Junkers | B25B 13/06 | 73/761 |
| 5,711,739 | A * | 1/1998 | Hashimoto | B23Q 5/048 | 475/263 |
| 5,950,509 | A * | 9/1999 | Doong | B25B 21/00 | 81/475 |
| 6,009,775 | A * | 1/2000 | Thompson | B25B 21/00 | 81/467 |
| 6,093,128 | A * | 7/2000 | Seith | F16H 3/54 | 475/258 |
| 6,258,090 | B1 * | 7/2001 | Jackson | A61B 17/7091 | 606/86 A |
| 6,308,598 | B1 * | 10/2001 | O'Neil | B25B 23/1415 | 81/439 |
| 6,349,625 | B1 * | 2/2002 | Poganski | B25B 23/141 | 81/475 |
| 6,802,680 | B1 * | 10/2004 | Rubenstein | F16B 31/021 | 411/908 |
| 7,032,481 | B2 * | 4/2006 | Li | B25B 23/1427 | 81/475 |
| 7,036,407 | B2 * | 5/2006 | Pyre | B25B 23/14 | 81/429 |
| 9,022,137 | B2 * | 5/2015 | Suzuki | B25B 23/141 | 81/475 |
| 9,051,972 | B2 * | 6/2015 | Garvey | F16D 7/024 | |
| 2006/0201282 | A1 * | 9/2006 | Lee | B25B 23/1427 | 81/58.3 |
| 2020/0271171 | A1 * | 8/2020 | Leung | F16D 7/002 | |

* cited by examiner

LOCKING DEVICES AND MECHANISMS FOR TORQUE-LIMITING DEVICES

REFERENCE TO RELATED APPLICATIONS

This application claims the priority benefit of U.S. Provisional Patent Application No. 63/458,797, filed on Apr. 12, 2023 and entitled "LOCKING DEVICES AND MECHANISMS FOR TORQUE-LIMITING DEVICES," which is fully incorporated by reference herein in its entirety.

BACKGROUND OF THE DISCLOSURE

Field of the Disclosure

The present disclosure is related generally to instruments for use in the medical field for surgical procedures, and specifically, to single-use or disposable torque-limiting drivers, torque-limiting attachments, and other tools with locking mechanisms to set a threshold torque for surgical applications.

Description of the Related Art

The use of torque-limiting devices is common in the medical field, especially during spinal and orthopedic surgery where a surgeon needs to fasten screws to secure surgical implants. The delivery of a precise amount of torque is critical in securing an implant or other surgical implement in the correct position without causing damage to the implant or the patient. In turn, it is critical for such torque-limiting devices to have an accurate and reliable locking mechanism to set the output torque precisely and reliably.

Presently, many torque-limiting devices use a locking mechanism comprising of a locknut that is set using a keyed locking process or procedure. However, these locking mechanisms are not continuously adjustable—meaning, there are discrete steps between each keyed interaction towards setting the output torque and making these mechanisms neither continuously adjustable nor simple to automate for production/manufacturing purposes. There is a need for a locking mechanism that is continuously adjustable, easy to assemble, and cost-effective for single-use or disposable torque-limiting devices.

SUMMARY OF THE DISCLOSURE

Some embodiments of a locking mechanism for torque-limiting devices, comprise a threaded component, wherein said threaded component is configured with a cylindrical hole that runs through said component; and a lock defining an opening at one end and a hole at the other end, wherein said opening is configured to enclose said threaded component and align said cylindrical hole of said threaded component and said hole of said lock.

Some embodiments of a locking mechanism for torque-limiting devices according to the present disclosure comprise a threaded component having a length, wherein said threaded component is configured with a recess running partially through the length; a lock defining an exterior that fits said recess of said threaded component; and a threaded socket defining an interior that fits said threaded component and said lock.

Also disclosed herein are torque-limiting assembly systems comprising: a speed reduction system; a locking mechanism comprising a threaded component having a cylindrical hole formed therethrough; and a lock having an opening at one end and a hole at the other end, wherein said opening is configured to enclose said threaded component and align said cylindrical hole of said threaded component and said hole of said lock; and a torque-limiting slip-clutch system.

This has outlined, rather broadly, the features and technical advantages of the present disclosure so that the detailed description that follows may be better understood. Additional features and advantages of the disclosure will be described below. It should be appreciated by those skilled in the art that this disclosure may be readily utilized as a basis for modifying or designing other structures for carrying out the same purposes of the present disclosure. It should also be realized by those skilled in the art that such equivalent constructions do not depart from the teachings of the disclosure as set forth in the appended claims. The novel features, which are believed to be characteristic of the disclosure, both as to its organization and method of operation, together with further features and advantages, will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

The features and advantages of the various exemplary embodiments will become apparent from the following detailed description when considered in conjunction with the accompanying drawings. Where possible, the same reference numerals and characters are used to denote like features, elements, components or portions of the inventive embodiments. It is intended that changes and modifications can be made to the described exemplary embodiments without departing from the true scope and spirit of the inventive embodiments described herein as defined by the claims.

DETAILED DESCRIPTION OF THE INVENTION

Figure 1A:
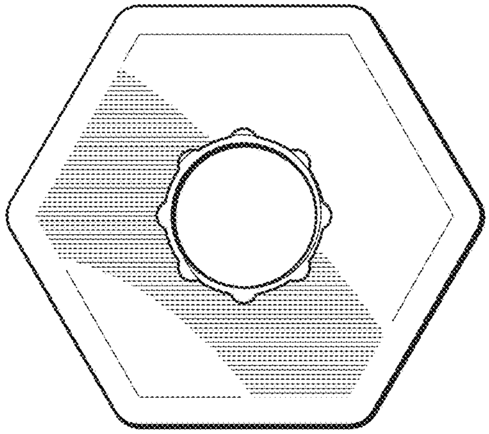
FIG. 1A shows a top view of an embodiment of a locking mechanism incorporating features of the present disclosure.

Embodiments incorporating features of the present disclosure include locking mechanisms for torque-limiting devices comprising a nut and a lock for the nut (e.g., a "jacket"). The nut and lock work together to create a friction-based lock.

Embodiments incorporating features of the present disclosure may be incorporated in torque-limiting assemblies within torque-limiting devices that utilize an elastic element. Embodiments of locking mechanisms disclosed herein set the output torque by biasing an elastic element of the torque-limiting system to a precise amount, and when that set-point is reached, the locking m creates a hard stop on the elastic element to keep it from creeping or moving. The hard stop provided by the locking mechanisms disclosed herein ensures the same torque set-point each time the tool or device actuates.

In the following detailed description, numerous specific details are set forth in order to provide a more thorough understanding of embodiments incorporating features of the present disclosure. However, it will be apparent to one skilled in the art that mechanisms, systems, devices and methods according to the present disclosure can be practiced without necessarily being limited to these specifically recited details.

Throughout this description, the preferred embodiment and examples illustrated should be considered as exemplars, rather than as limitations on the present invention. As used herein, the term "invention," "device," "method," "disclosure," "present invention," "present device," "present method," or "present disclosure" refers to any one of the embodiments of the invention described herein, and any equivalents. Furthermore, reference to various feature(s) of the "invention," "device," "method," "disclosure," "present invention," "present device," "present method," or "present disclosure" throughout this document does not mean that all claimed embodiments or methods must include the referenced feature(s).

It is also understood that when an element or feature is referred to as being "on" or "adjacent" to another element or feature, it can be directly on or adjacent the other element or feature or intervening elements or features may also be present. It is also understood that when an element is referred to as being "attached," "connected" or "coupled" to another element, it can be directly attached, connected or coupled to the other element or intervening elements may be present. In contrast, when an element is referred to as being "directly attached," "directly connected" or "directly coupled" to another element, there are no intervening elements present.

Relative terms such as "outer," "above," "lower," "below," "horizontal," "vertical" and similar terms, may be used herein to describe a relationship of one feature to another. It is understood that these terms are intended to encompass different orientations in addition to the orientation depicted in the figures.

Although the terms first, second, etc. may be used herein to describe various elements or components, these elements or components should not be limited by these terms. These terms are only used to distinguish one element or component from another element or component. Thus, a first element or component discussed below could be termed a second element or component without departing from the teachings of the present invention. As used herein, the term "and/or" includes any and all combinations of one or more of the associated list items.

The terminology used herein is for describing particular embodiments only and is not intended to be limiting of the invention. As used herein, the singular forms "a," "an," and "the" are intended to include the plural forms as well, unless the context clearly indicates otherwise. It will be further understood that the terms "comprises," "comprising," "includes," "including," "has," "having," and similar terms, when used herein, specify the presence of stated features, integers, steps, operations, elements, and/or components, but do not preclude the presence or addition of one or more other features, integers, steps, operations, elements, components, and/or groups thereof.

Embodiments of the invention are described herein with reference to different views and illustrations that are schematic illustrations of idealized embodiments of the invention. As such, variations from the shapes of the illustrations as a result, for example, of manufacturing techniques and/or tolerances are expected. Embodiments of the invention should not be construed as limited to the particular shapes of the regions illustrated herein but are to include deviations in shapes that result, for example, from manufacturing. Like elements among embodiments are referenced herein with the same reference numerals, except where differences are articulated.

Embodiments incorporating features of the present disclosure can be single-use or disposable. One such locking mechanism comprises at least the following components: a threaded component and a lock defining an interior that is configured to fit the threaded component. The lock ensures a threshold or set-point torque.

Figure 2:
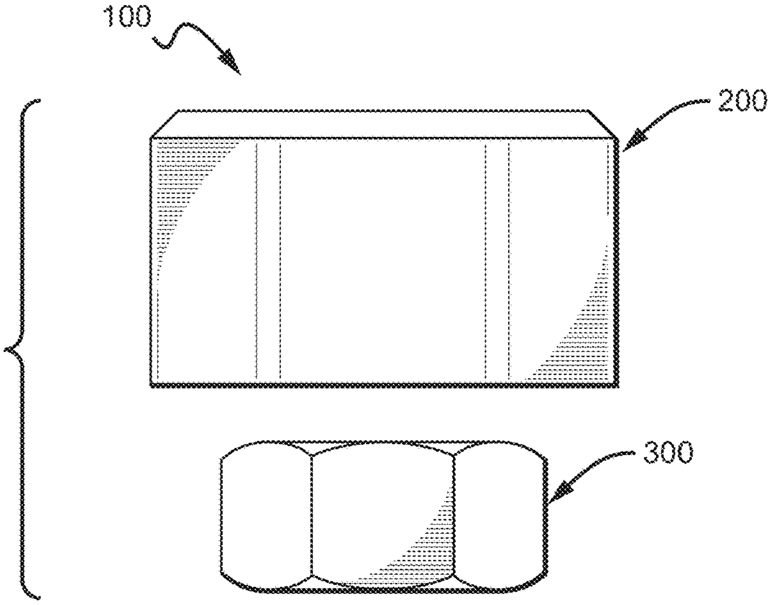
FIG. 2 shows an exploded view of the embodiment of FIG. 1A.
Figure 3:
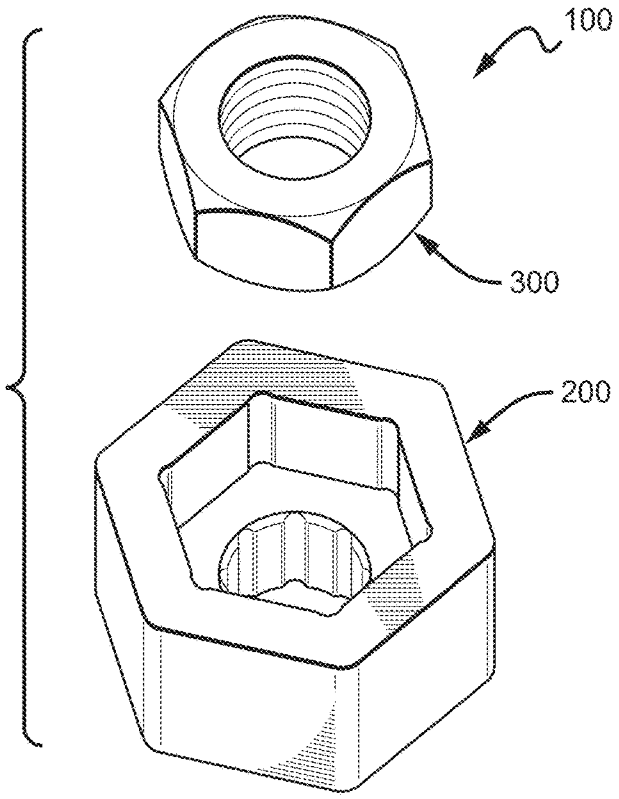
FIG. 3 shows another exploded view of the embodiment of FIG. 1A.

FIGS. 1A-1E show various perspective views of one embodiment of a locking mechanism 100, incorporating features of the present disclosure. The locking mechanism 100 shown comprises a lock 200 and a threaded component 300. The threaded component 300 may be configured with a vertical cylindrical hole 302 that runs through the threaded component 300 defining openings on both sides of the threaded component 300. The threaded component 300 may be a nut or screw. In some embodiments, threaded component 300 may be configured with threads axially formed 304 within the vertical cylindrical hole 302. In other embodiments, the threaded component may be configured with threads axially formed along the exterior of the threaded component 300. FIGS. 2 and 3 also show exploded views of locking mechanisms 100 according to the present disclosure.

The lock 200 is configured to house the threaded component 300 and may have openings on top and bottom faces. At one end, which is considered to be the top or upper end, the lock 200 may have a hole 204 with a diameter that is the same diameter as the hole 302 of the threaded component 300. It is understood, however, that this hole 204 may also have a different diameter that is smaller or larger than the hole of the threaded component 300. An opening 206 on the other end, which is considered the bottom or lower end, of the lock 200 is configured to be the same size and shape as the threaded component 300, such that the threaded component 300 may be inserted or placed into the lock 200 via the opening 206.

Figure 1B:
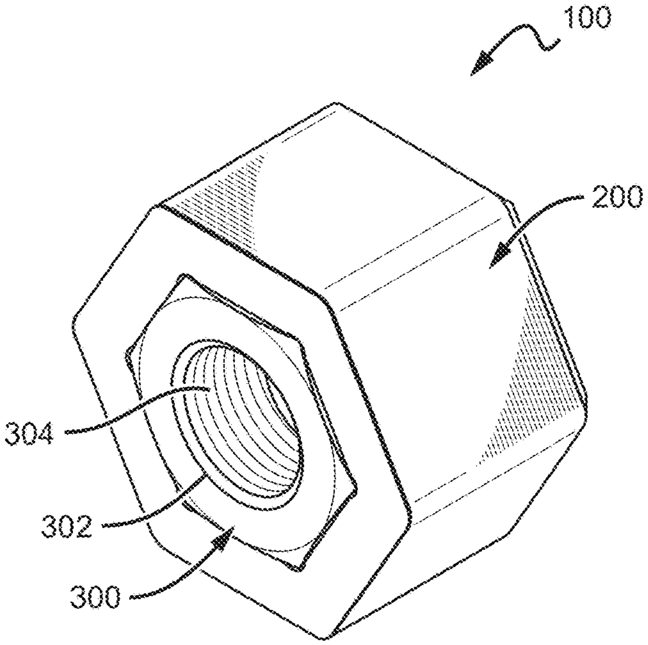
FIG. 1B shows a bottom perspective view of the embodiment of FIG. 1A.
Figure 1C:
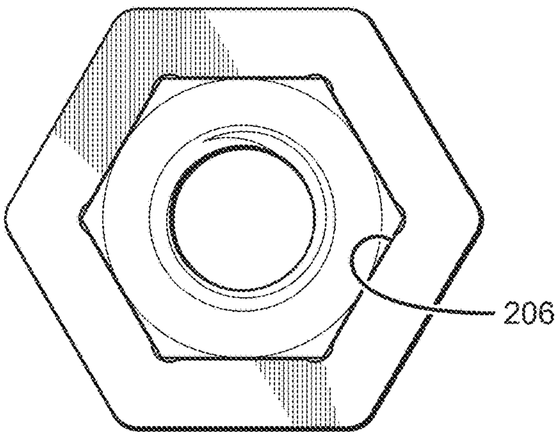
FIG. 1C shows a bottom view of the embodiment of FIG. 1A.
Figure 1D:
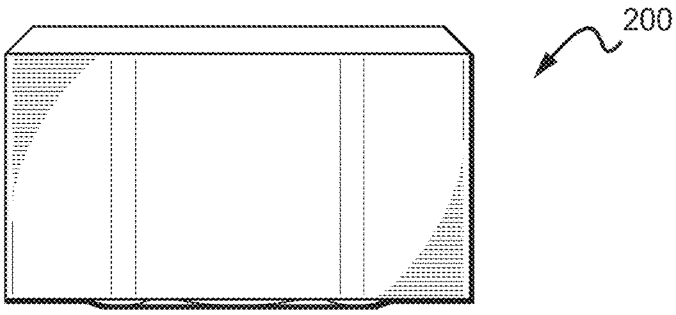
FIG. 1D shows a right side view of the embodiment of FIG. 1A.
Figure 1E:
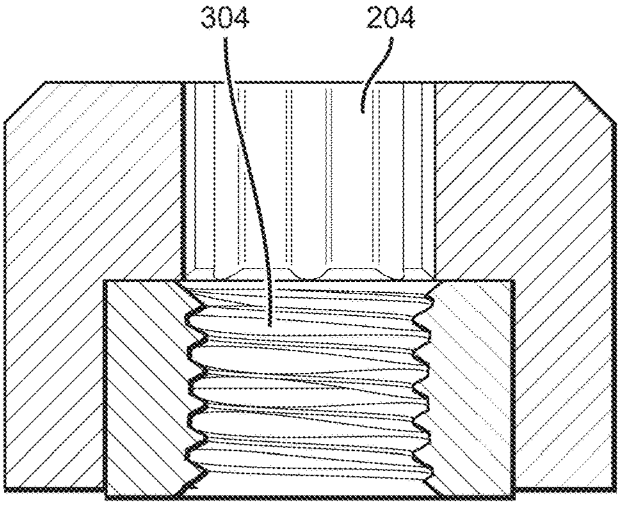
FIG. 1E shows a sectional view of the embodiment of FIG. 1A.
Figure 7:
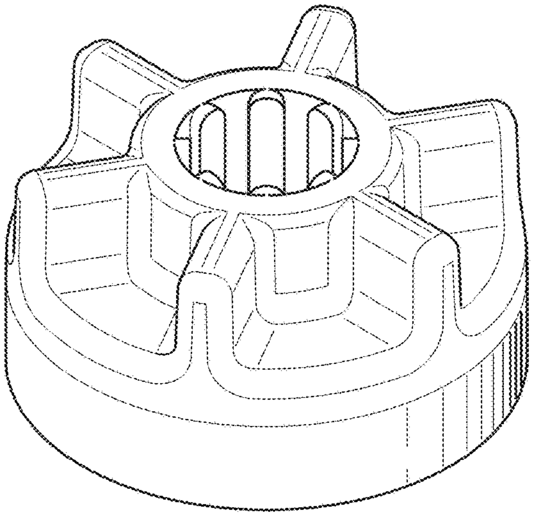
FIG. 7 shows top perspective view of another embodiment of a lock or jacket of a locking mechanism incorporating features of the present disclosure.
Figure 8:
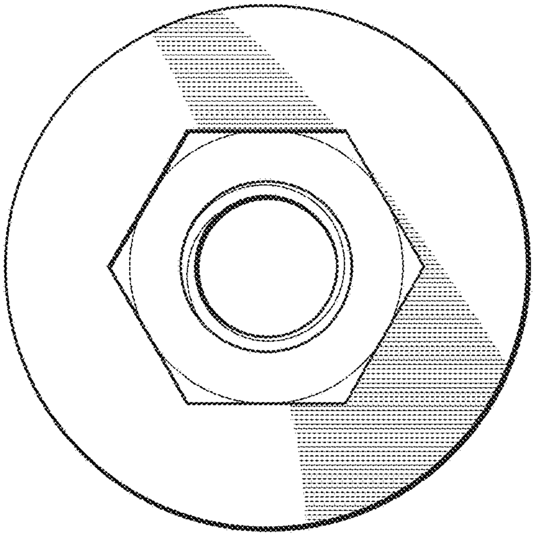
FIG. 8 shows a bottom view of another embodiment of a locking mechanism incorporating features of the present disclosure.
Figure 9A:
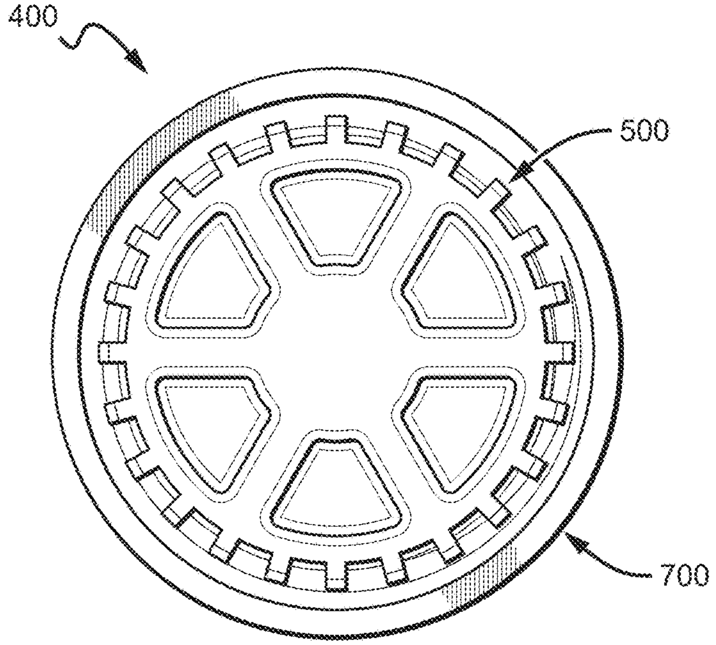
FIG. 9A shows a top view of another embodiment of a locking mechanism incorporating features of the present disclosure.
Figure 9B:
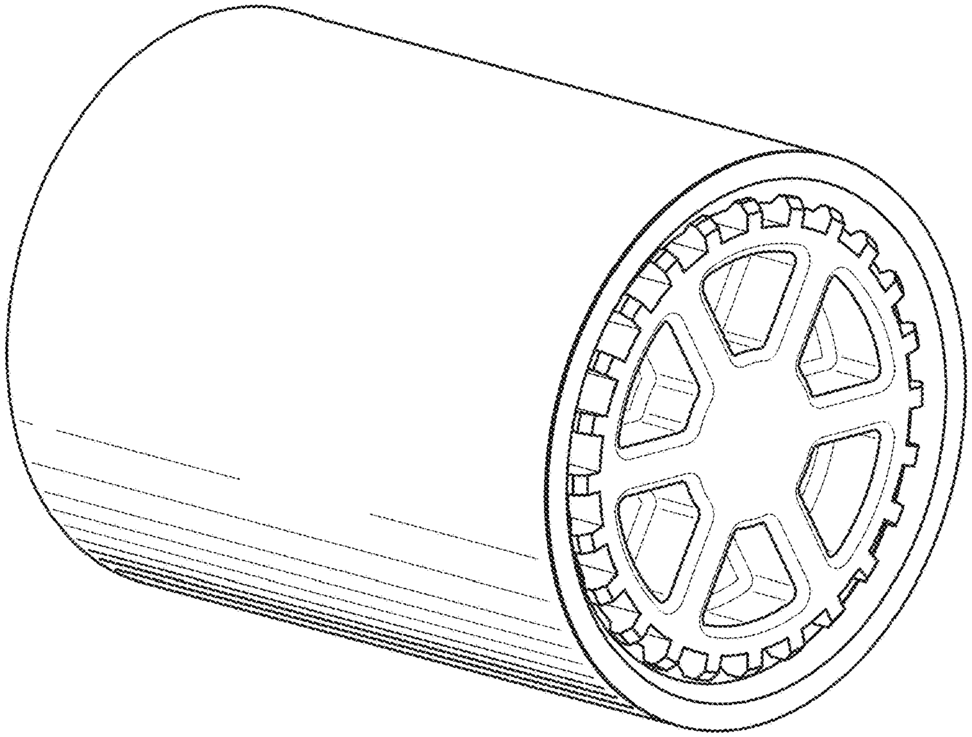
FIG. 9B shows a top perspective view of the embodiment of FIG. 9A.
Figure 9C:
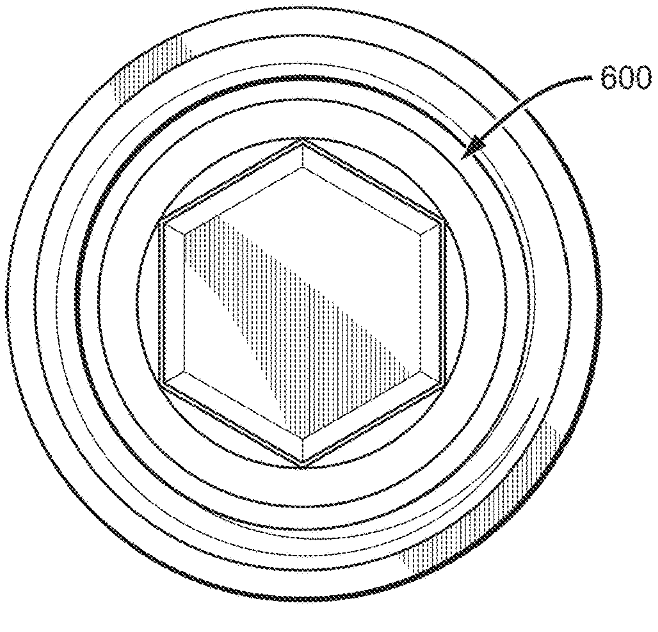
FIG. 9C shows a bottom view of the embodiment of FIG. 9A.
Figure 9D:
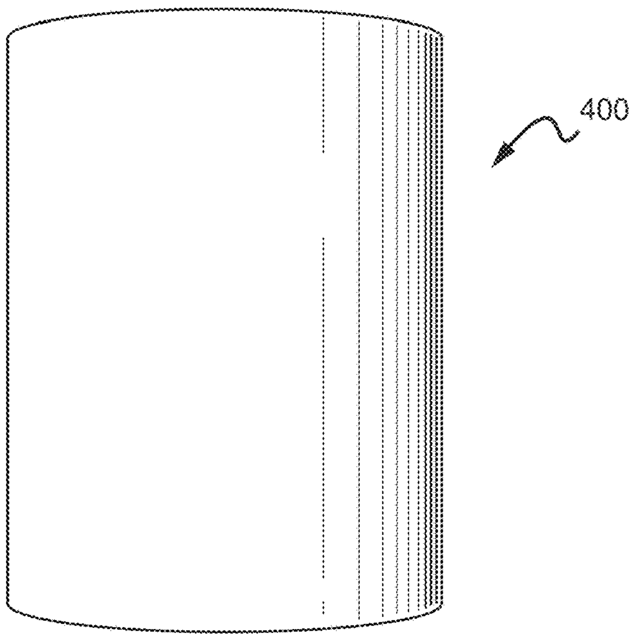
FIG. 9D shows a side view of the embodiment of FIG. 9A.
Figure 9E:
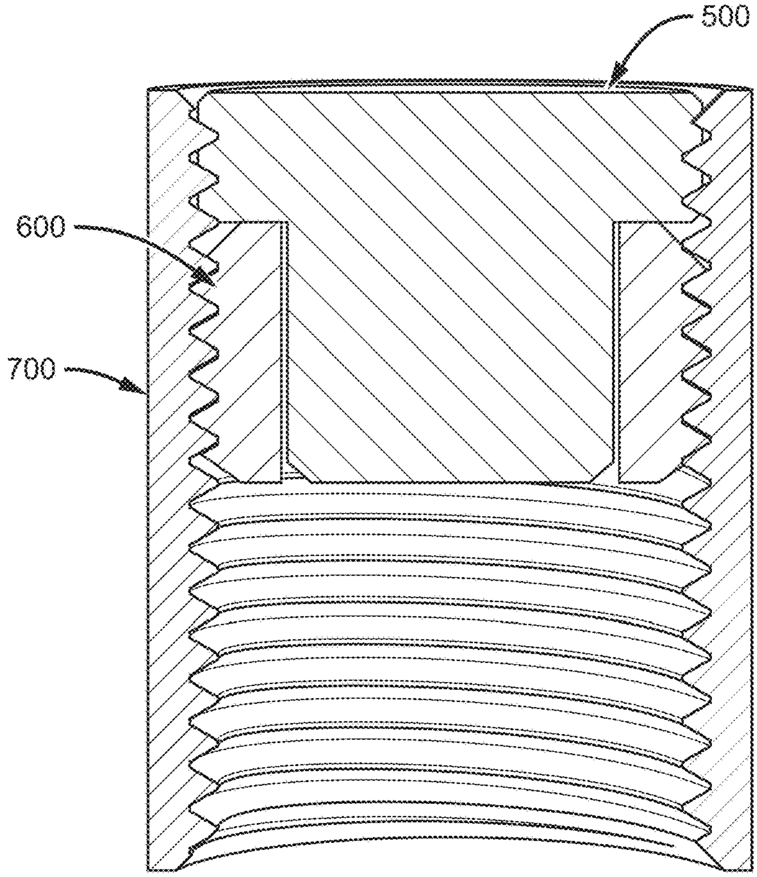
FIG. 9E shows a side sectional view of the embodiment of FIG. 9A.

Although the locking mechanism 100 shown in FIGS. 1A-1C generally has a hexagonal shape, it is understood that many different shapes are possible, such as, for example, circular or square shapes. The shape of the lock 200 may be different than the shape of the threaded component 300 so long as the opening 206 on the bottom end is configured to house the threaded component 300. Additionally, while the locking 200 shown in FIGS. 1A-1C generally comprises sides perpendicular to the top and bottom faces, it is understood that said sides may be formed at an angle relative to said faces. FIGS. 7 and 8 exemplify a alternative few of many shapes and configurations for the lock 200 and the locking mechanism 100.

Figure 4A:
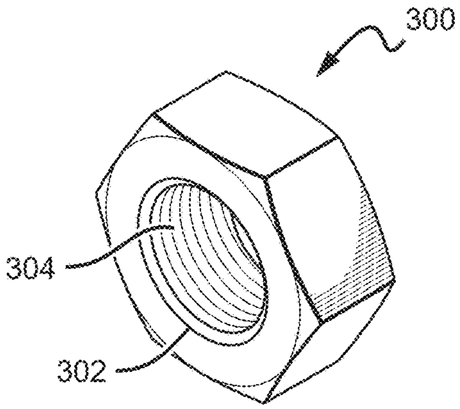
FIGS. 4A-4B show top front perspective and front views of a nut component of an embodiment of a locking mechanism incorporating features of the present disclosure.
Figure 4B:
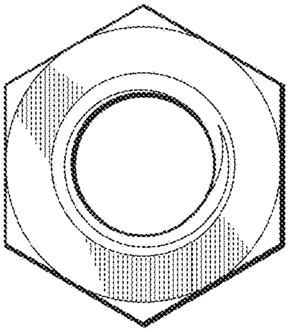

FIGS. 4A-4B show various views of one embodiment of a threaded component 300 according to the present disclosure. The threaded component 300 shown is a threaded nut, but many types of threaded components 300 are possible. For example, but not in any limiting fashion, an interference thread nut or a setscrew may be used as threaded components 300. The threaded component 300 may be made of one or more materials, such as, for example, steel, metallic alloys, or other materials or coatings as would be understood by one of skill in the art. The threaded component 300 may also have threading in the interior or the exterior. In other embodiments, the threaded component 300 may have distorted threads.

Figure 5A:
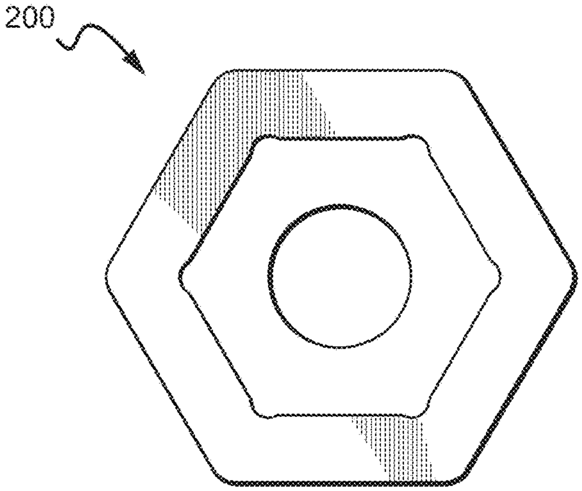
FIG. 5A shows a bottom view of a lock or jacket of an embodiment of a locking mechanism incorporating features of the present disclosure.
Figure 5B:
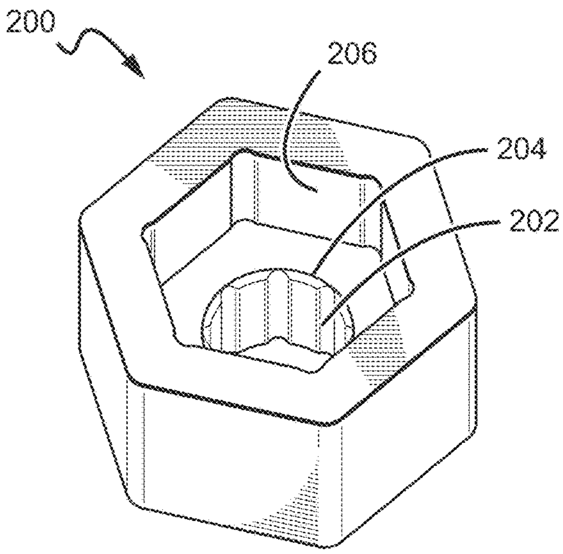
FIG. 5B shows a bottom perspective view of the lock or jacket of the embodiment of FIG. 5A.
Figure 5C:
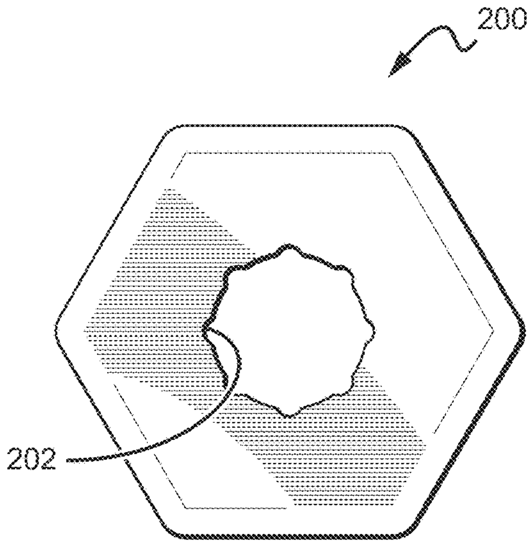
FIG. 5C shows a top view of the lock or jacket of the embodiment of FIG. 5A.
Figure 5D:
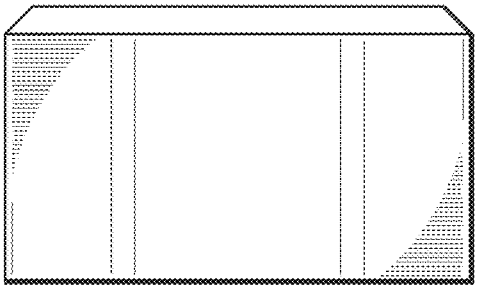
FIG. 5D shows a right side view of the lock or jacket of the embodiment of FIG. 5A.
Figure 5E:
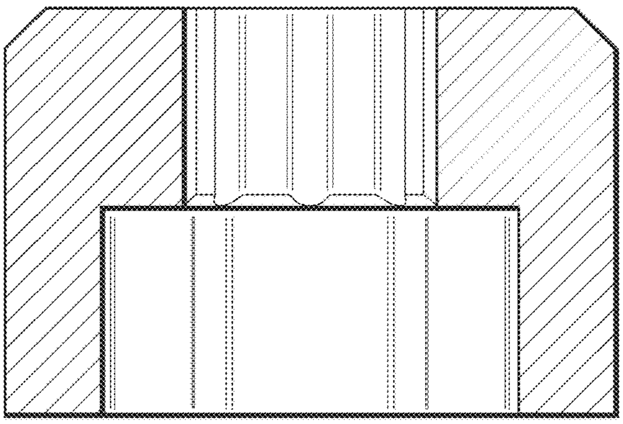
FIG. 5E shows a sectional view of the lock or jacket of the embodiment of FIG. 5A.

Various views of one embodiment of a lock 200 according to the present disclosure can be seen in FIGS. 5A-5E. The lock 200 shown features ribbing or threading 202 in the hole 204 located on the top end of the lock 200. Views and examples of this ribbing 202 are shown in FIGS. 5B and 5E. In some embodiments, the ribbing 202 causes friction between the locking mechanism 100 and a threaded shaft of a torque-limiting device, thereby locking the mechanism 100 in place. The lock 200 may be made of one or more different materials, such as polymer resins, composite-filled polymer resins, metals, metallic alloys, or other materials as would be understood by one of skill in the art.

Figure 10:
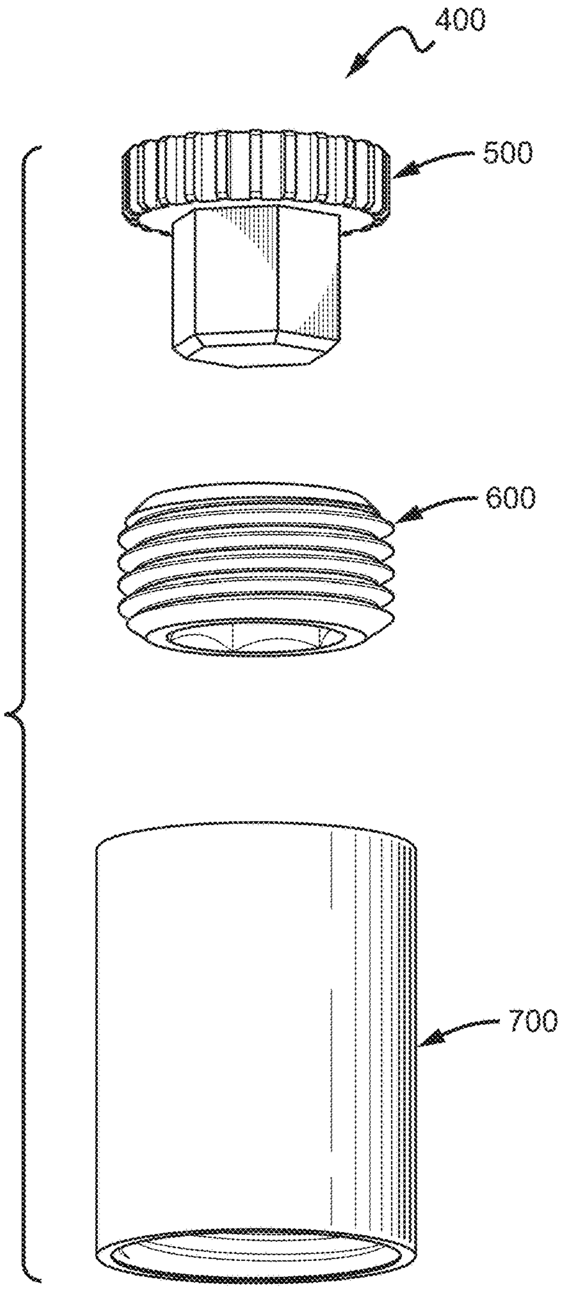
FIG. 10 shows an exploded view of the embodiment of FIG. 9A.
Figure 11:
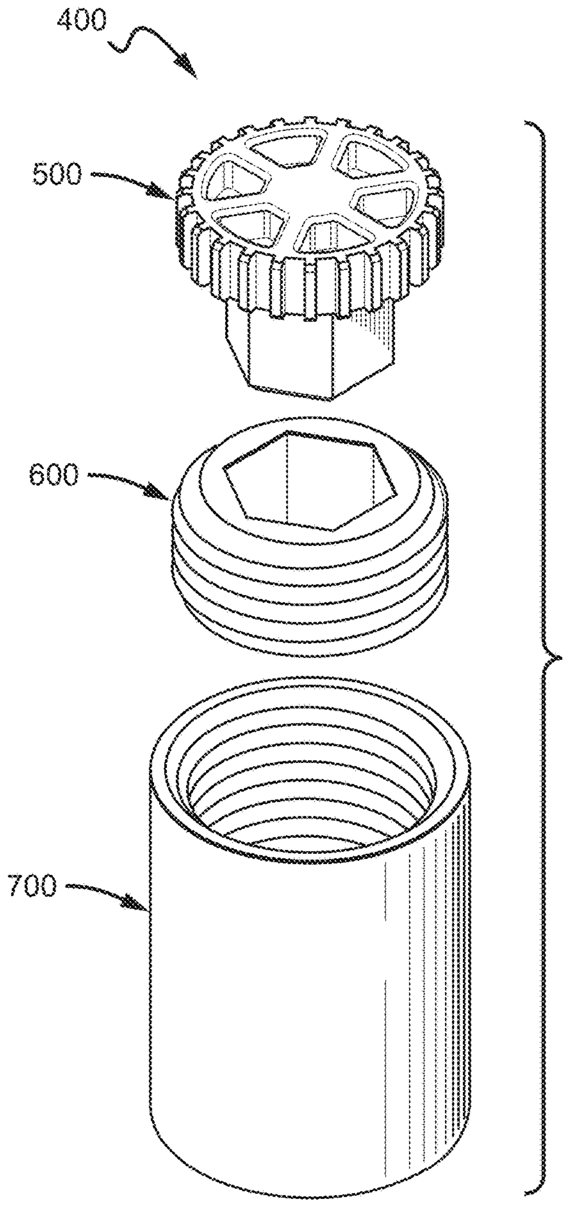
FIG. 11 shows another exploded view of the embodiment of FIG. 9A.

FIGS. 9A-9E show various perspective views of another embodiment a of locking mechanism 400, incorporating features of the present disclosure. The locking mechanism 400 comprises a lock 500, a threaded component 600, and a threaded socket 700. The threaded component 600 comprises a vertical opening 602. The vertical opening 602 may extend through the entirety of threaded component 600, defining a hole, or it may extend partially through the threaded component 600, defining a cavity. Although the vertical opening 602 is shown with a generally hexagonal shape, it is understood that other shapes are possible, such as square, round, octagonal, and other shapes known to one of skill in the art. In some embodiments, the threaded component 600 may be a setscrew. The threaded component 600 comprises threads 604. FIGS. 10 and 11 show also show exploded views of locking mechanism 400 shown in FIGS. 9A-9E according to the present disclosure.

This embodiment of the lock 500 comprises a body 504 configured to mate with the vertical opening 602 of the threaded component 600. The body 504 is configured to be the same size and shape of the vertical opening 602, such that the body may be inserted or placed in the threaded component 600 via the opening 602. Although the locking mechanism 400 shown in FIGS. 9A-9C generally has a hexagonal shape, it is understood that many different shapes are possible such as circular or square shapes.

Figure 12A:
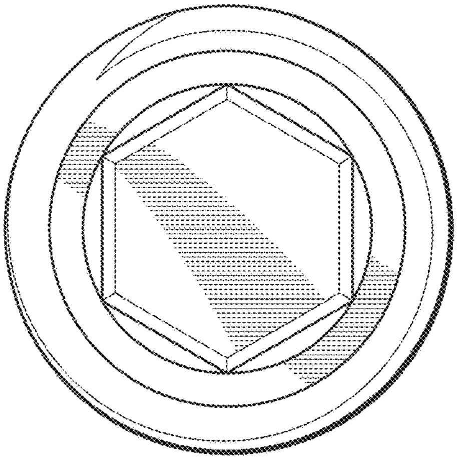
FIGS. 12A-12B show top and top perspective views of the threaded component of the locking mechanism shown in FIG. 9A.
Figure 12B:
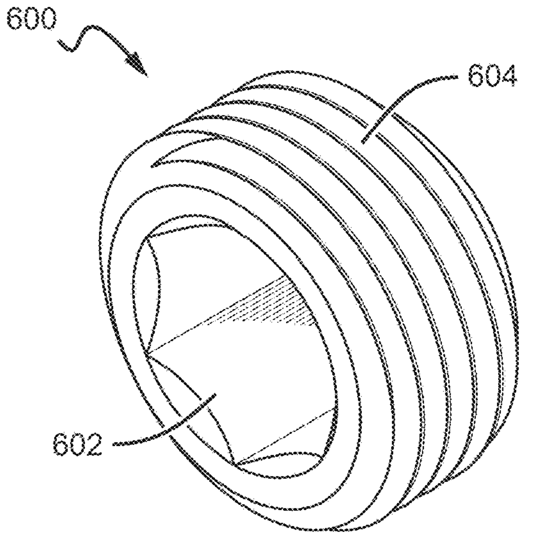

FIGS. 12A-12B show various views of one embodiment of a threaded component 600 according to the present disclosure. The threaded component 600 shown is a setscrew, but many types of threaded components are possible. For example, and not by way of limitation, the threaded component may be a threaded nut or an interference thread nut. The threaded component 600 may be made of one or more materials, such as, steel, metallic alloys, or other materials or coatings as would be understood by one of skill in the art. The threaded component 600 may also have threading in the interior or the exterior. In other embodiments, the threaded component 600 may have distorted threads.

Figure 13A:
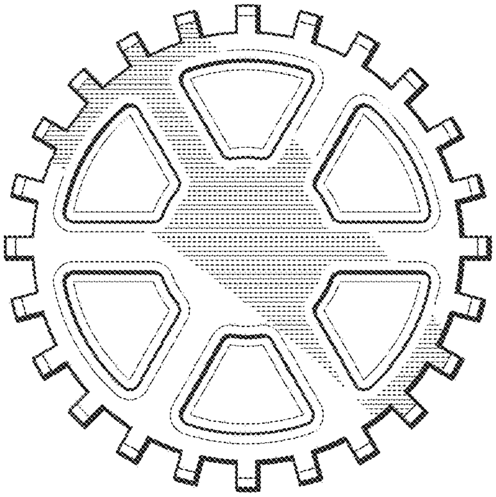
FIG. 13A shows a top view of the lock of the locking mechanism shown in FIG. 9A.
Figure 13B:
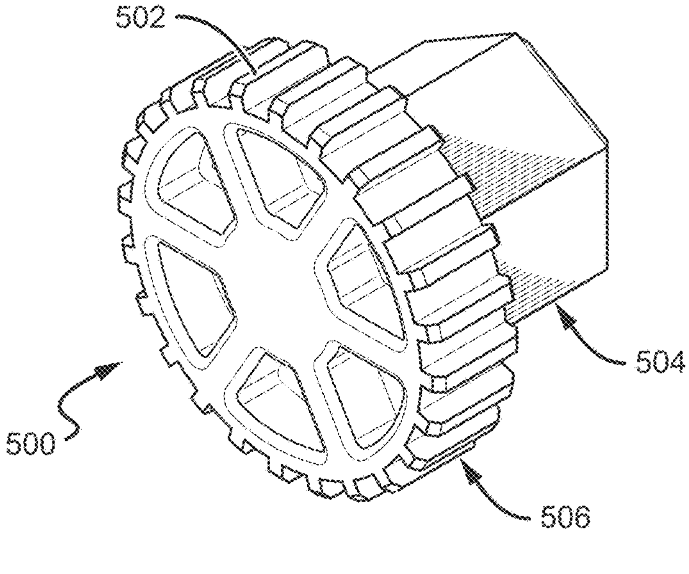
FIG. 13B shows a top perspective view of the lock of the locking mechanism shown in FIG. 9A.
Figure 13C:
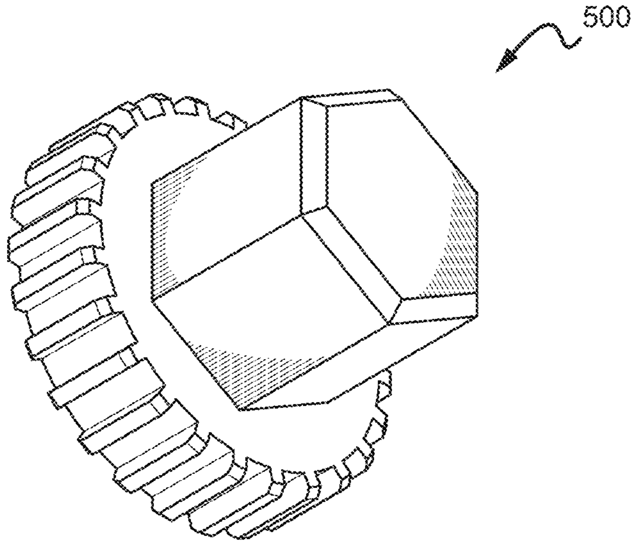
FIG. 13C shows a bottom perspective view of the lock of the locking mechanism shown in FIG. 9A.
Figure 13D:
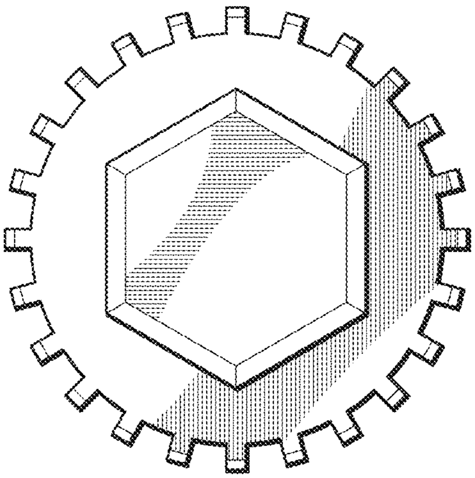
FIG. 13D shows a bottom view of the lock of the lock of the locking mechanism shown in FIG. 9A.
Figure 13E:
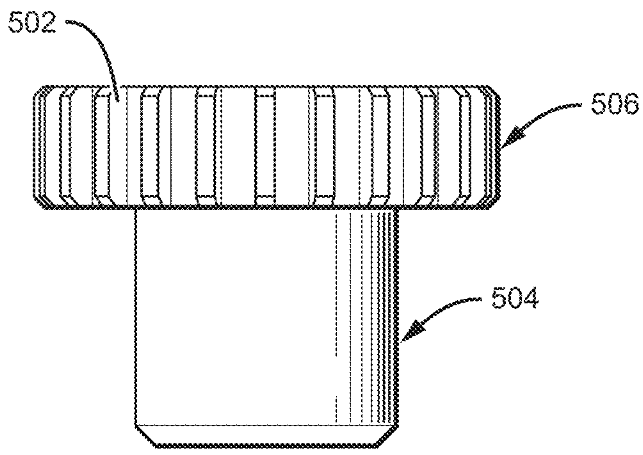
FIG. 13E shows a right side view of the lock of the lock of the locking mechanism shown in FIG. 9A.

Various views of one embodiment of a lock 500 according to the present disclosure can be seen in FIGS. 13A-13E. The lock 500 comprises a head 506 and a body 504. The head 506 comprises ribbing or threading 502 on its outer circumference. Views and examples of this ribbing or threading are shown in FIGS. 13B and 13E. In some embodiments, the ribbing 502 causes friction between the locking mechanism 400 and a threaded shaft of a torque-limiting device, thereby locking the mechanism 400 in place. The lock 500 may be made of one or more different materials, such as polymer resins, composite-filled polymer resins, metals, metallic alloys, or other materials as would be understood by one of skill in the art.

Figure 14A:
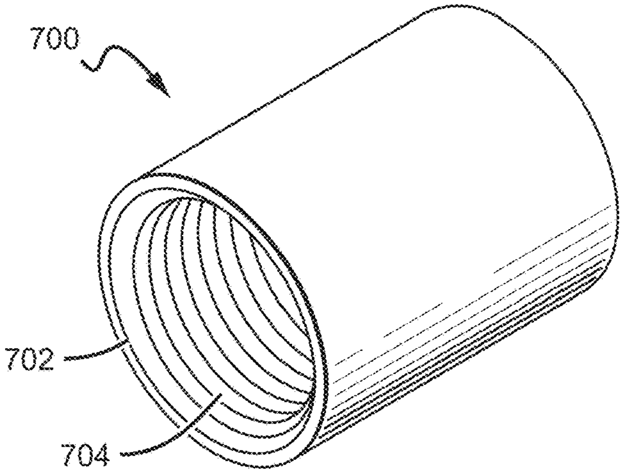
FIG. 14A shows a right side perspective view of the threaded socket of the locking mechanism shown in FIG. 9A.
Figure 14B:
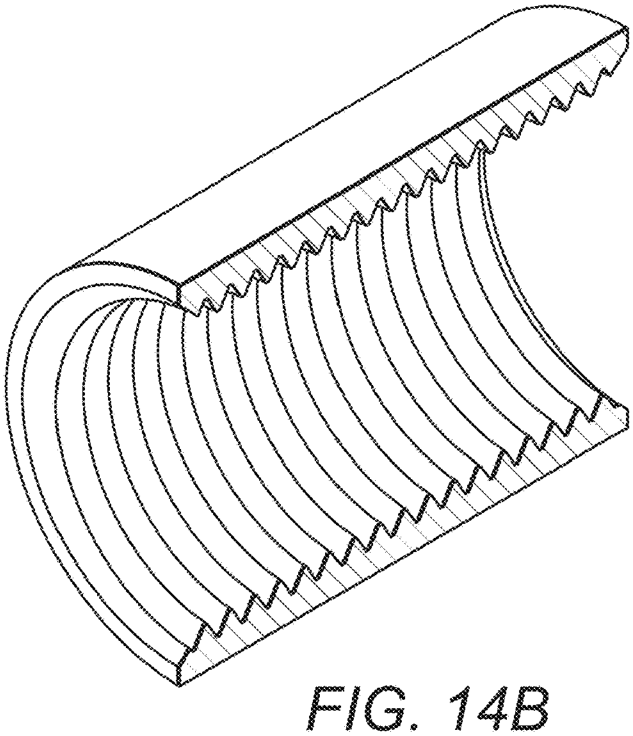
FIG. 14B shows a sectional view of the threaded socket of the locking mechanism shown in FIG. 9A.
Figure 14C:
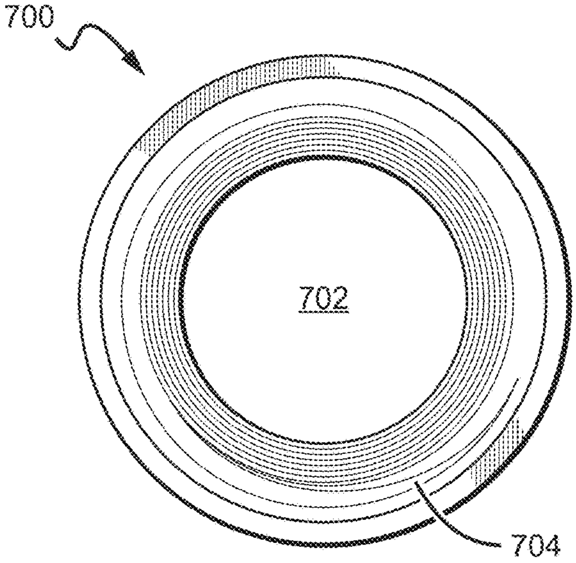
FIG. 14C shows a top view of the threaded socket of the locking mechanism shown in FIG. 9A.

FIGS. 14A-14C show various perspective views of a threaded socket 700 according to the present disclosure. The threaded socket 700 comprises a hole 702 that passes through the entire threaded socket 700 and threads 704. The hole 702 may have the same diameter as the outer diameter of the threaded component 600 and may have a diameter smaller than the diameter of the head 506. In some embodiments, the threaded socket 700 comprises the threaded shaft of a torque-limiting device. In some embodiments, the ribbing or threading 502 cause friction with the threads 704, thereby locking the lock 500 with respect to the threaded socket 700. The threaded socket 700 may be made of one or more different materials, such as polymer resins, composite-filled polymer resins, metals, metallic alloys, or other materials as would be understood by one of skill in the art.

Embodiments of locking mechanisms disclosed herein may also incorporate an elastic interface between the threaded component 300 and the lock 200 or between the threaded component 600 and the lock 500. One of many benefits of including an elastic interface is vibration reduction between the two components.

Figure 6:
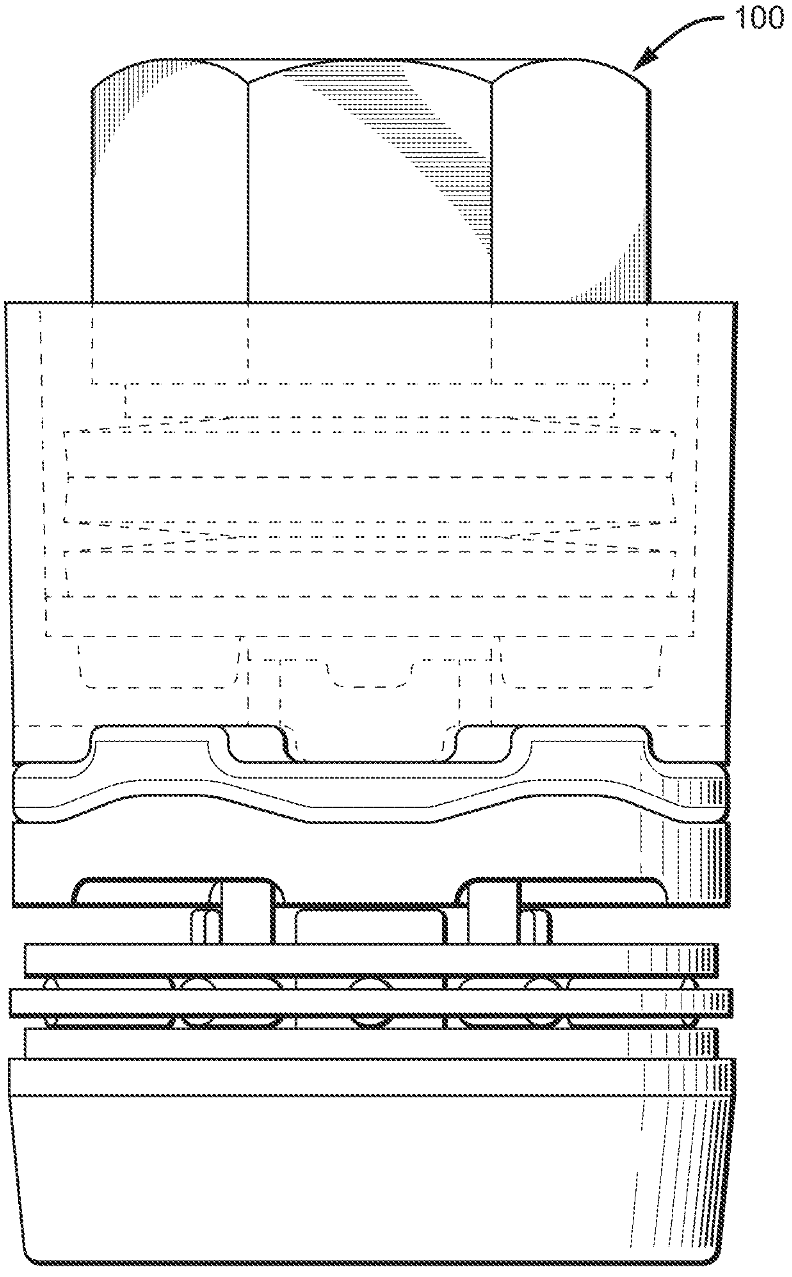
FIG. 6 shows a front view of the embodiment of a locking mechanism shown in FIG. 1A, incorporated into a torque-limiting assembly, with the clutch carrier of the torque-limiting assembly transparent in order to better view the interaction between the locking mechanism and the other components of the torque-limiting assembly.

Embodiments of locking mechanisms 100 and 400 disclosed herein may be found in torque-limiting assemblies, which are in turn found within torque-limiting devices. In one example, a torque-limiting assembly may comprise: a speed reduction system, a locking mechanism, and a torque-limiting slip-clutch system. It is understood that many configurations of torque-limiting assemblies are possible. Embodiments of locking mechanisms disclosed herein work together with the elastic or spring component of torque-limiting assemblies to set a threshold or set-point output torque for the device. An example of how locking mechanisms 100 and 400 according to the present disclosure may work together with an elastic or spring component of torque-limiting assemblies is shown in FIG. 6. In FIG. 6, the locking mechanism 100 sits on top of a composition of flat and Belleville spring washers (the elastic element), which act as a stiff spring. The locking mechanism 100 biases the washers to a set-point or threshold torque and locks the washers in place so that the torque-limiting device ultimately applies the correct amount of force. It is understood that the locking mechanism 400 may be substituted for locking mechanism 100 in FIG. 6.

At least one advantage of the locking devices and mechanisms incorporating features of the present disclosure is axial load isolation between threaded component 300 or 600 and the lock 200 or 500, respectively, allowing the torque-limiting device that incorporates the locking mechanism to go to a higher torque threshold.

It is understood that while the present application is primarily directed to torque-limiting mechanisms utilized with medical instruments, it is understood that torque-limiting or ratcheting mechanisms incorporating features of the present disclosure can also be utilized in any other tool that can potentially benefit from them, for example, basic screwdrivers for use with construction projects.

The various exemplary inventive embodiments described herein are intended to be merely illustrative of the principles underlying the inventive concept. It is therefore contemplated that various modifications of the disclosed embodiments will without departing from the inventive spirit and scope be apparent to persons of ordinary skill in the art. They are not intended to limit the various exemplary inventive embodiments to any precise form described. Other variations and inventive embodiments are possible in light of the above teachings, and it is not intended that the inventive scope be limited by this specification, but rather by the claims following herein.

Although the present invention has been described in detail with reference to certain preferred configurations thereof, other versions are possible. Embodiments of the present invention can comprise any combination of compatible features shown in the various figures, and these embodiments should not be limited to those expressly illustrated and discussed. Therefore, the spirit and scope of the invention should not be limited to the versions described above. Moreover, it is contemplated that combinations of features, elements, and steps from the appended claims may be combined with one another as if the claims had been written in multiple dependent form and depended from all prior claims. Combination of the various devices, components, and steps described above and in the appended claims are within the scope of this disclosure. The foregoing is intended to cover all modifications and alternative constructions falling within the spirit and scope of the invention.

We claim:

1. A locking mechanism for torque-limiting devices, comprising:
- a threaded component, wherein said threaded component is configured with a cylindrical hole that runs through said component;
- a lock defining an opening at one end and a hole at the other end, wherein said opening is configured to enclose said threaded component and align said cylindrical hole of said threaded component and said hole of said lock; and
- an elastic component between said threaded component and said lock.

2. The locking mechanism of claim 1, wherein said opening of said lock is configured with the same shape as the exterior of said threaded component.

3. The locking mechanism of claim 1, wherein the depth of said opening of said lock is sufficiently deep to engage said threaded component.

4. The locking mechanism of claim 1, wherein the outside of said threaded component is hexagonally shaped.

5. The locking mechanism of claim 4, wherein said opening of said lock is hexagonally shaped.

6. The locking mechanism of claim 1, wherein said opening of said lock is configured to frictionally interfere with said threaded component.

7. The locking mechanism of claim 1, wherein said threaded component is an interference thread nut.

8. The locking mechanism of claim 1, wherein said hole of said lock is configured with ribbing.

9. The locking mechanism of claim 1, wherein said lock comprises a polymer.

10. The locking mechanism of claim 1, wherein said threaded component comprises a metal.

11. A locking mechanism for torque-limiting devices, comprising:
- a threaded component having a length, wherein said threaded component is configured with a recess running at least partially through said length and interior threads;
- a lock defining an exterior that fits said recess of said threaded component; and
- a threaded socket defining an interior that fits said threaded component and said lock.

12. A torque-limiting system comprising:
- a speed reduction system having an output shaft;
- a torque-limiting slip-clutch system connected to said output shaft; and
- a locking mechanism connected to said torque-limiting slip-clutch system and comprising:
  - a threaded component having a cylindrical hole formed therethrough; and a lock having an opening at one end and a hole at the other end, wherein said opening is configured to enclose said threaded component and align said cylindrical hole of said threaded component and said hole of said lock, wherein upon the application of a predetermined torque to said output shaft, said threaded component and said lock of said locking mechanism frictionally lock, causing said torque-limiting slip-clutch system to slip.

13. A locking mechanism for torque-limiting devices, comprising:

a threaded component, wherein said threaded component is configured with a cylindrical hole that runs through said component; and a lock defining an opening at one end and a threaded hole at the other end, wherein said opening is configured to enclose said threaded component and align said cylindrical hole of said threaded component and said hole of said lock.

14. A locking mechanism for torque-limiting devices, comprising:

a set screw having a length, wherein said set screw is configured with a recess running at least partially through said length;

a lock defining an exterior that fits said recess of said set screw; and a threaded socket defining an interior that fits said set screw and said lock.

15. The locking mechanism of claim 14, wherein said set screw comprises threading on its exterior.

* * * * *